(12) United States Patent
Mercando et al.

(10) Patent No.: US 6,201,033 B1
(45) Date of Patent: *Mar. 13, 2001

(54) REACTIVE CATALYST COMPOSITIONS FOR IMPROVING WATER BLOWN POLYURETHANE FOAM PERFORMANCE

(75) Inventors: Lisa Ann Mercando, Pennsburg; Mark Leo Listemann; Michael John Kimock, both of Kutztown, all of PA (US)

(73) Assignee: Air Products and Chemical, Inc., Allentown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/256,932

(22) Filed: Feb. 24, 1999

Related U.S. Application Data

(63) Continuation-in-part of application No. 08/879,472, filed on Jun. 20, 1997, which is a continuation-in-part of application No. 08/850,985, filed on May 6, 1997, now Pat. No. 5,824,711, which is a continuation-in-part of application No. 08/851,652, filed on May 6, 1997, now Pat. No. 5,756,557.

(51) Int. Cl.⁷ ..................................................... C08J 9/04
(52) U.S. Cl. ............................ 521/129; 521/155; 521/170
(58) Field of Search .................................. 521/129, 155, 521/170

(56) References Cited

U.S. PATENT DOCUMENTS

| | | |
|---|---|---|
| 4,194,069 | 3/1980 | Speranza et al. . |
| 4,242,467 | 12/1980 | Zimmerman . |
| 4,330,656 | 5/1982 | Grogler et al. . |
| 4,348,536 | 9/1982 | Blahak et al. . |
| 4,644,017 | 2/1987 | Haas et al. . |

FOREIGN PATENT DOCUMENTS

| | | |
|---|---|---|
| 2061168 | 8/1918 | (CA) . |
| 3027796 | 2/1918 | (DE) . |

OTHER PUBLICATIONS

Dabco®B–16 Catalyst Product Bulletin Wall Chart "Air Products Polyurethane Additives" with listing of Dabco®B–16 Catalyst (1988).

*Primary Examiner*—John M. Cooney, Jr.
(74) *Attorney, Agent, or Firm*—Michael Leach

(57) ABSTRACT

The present invention provides a reactive catalyst composition for making a water blown flexible polyurethane foam. The catalyst composition comprises a tertiary amino alkyl urea and/or bis(tertiary amino alkyl) urea in combination with either a tertiary amine gelling catalyst or a tertiary amine blowing catalyst. The use of such catalyst composition improves the physical properties of the polyurethane foam.

6 Claims, No Drawings

REACTIVE CATALYST COMPOSITIONS FOR IMPROVING WATER BLOWN POLYURETHANE FOAM PERFORMANCE

CROSS-REFERENCE TO RELATED APPLICATIONS

This application is a continuation-in-part of application Ser. No. 08/879,472 filed Jun. 20, 1997 which is a continuation-in-part of both application Ser. No. 08/850,985 filed May 6, 1997 entitled "N,N,N'-Trimethylbis(aminoethyl)ether Substituted Urea Compositions For The Production Of Polyurethanes", now U.S. Pat. No. 5,824,711, and application Ser. No. 08/851,652 filed May 6, 1997 entitled "Aminomethyl Pyrrolidine Urea Compositions For The Production Of Polyurethanes", now U.S. Pat. No. 5,756,557.

BACKGROUND OF THE INVENTION

The present invention relates to tertiary amine catalysts for producing polyurethane foam.

Polyurethane foams are widely known and used in automotive, housing and other industries. Such foams are produced by reaction of a polyisocyanate with a polyol in the presence of various additives. One such additive is a chlorofluorocarbon (CFC) blowing agent which vaporizes as a result of the reaction exotherm, causing the polymerizing mass to form a foam. The discovery that CFCs deplete ozone in the stratosphere has resulted in mandates diminishing CFC use. Production of water-blown foams, in which blowing is performed with $CO_2$ generated by the reaction of water with the polyisocyanate, has therefore become increasingly important. Tertiary amine catalysts are typically used to accelerate blowing (reaction of water with isocyanate to generate $CO_2$) and gelling (reaction of polyol with isocyanate).

The ability of the tertiary amine catalyst to selectively promote either blowing or gelling is an important consideration in selecting a catalyst for the production of a particular polyurethane foam. If a catalyst promotes the blowing reaction to a too high degree, much of the $CO_2$ will be evolved before sufficient reaction of isocyanate with polyol has occurred, and the $CO_2$ will bubble out of the formulation, resulting in collapse of the foam. A foam of poor quality will be produced. In contrast, if a catalyst too strongly promotes the gelling reaction, a substantial portion of the $CO_2$ will be evolved after a significant degree of polymerization has occurred. Again, a poor quality foam, this time characterized by high density, broken or poorly defined cells, or other undesirable features, will be produced.

Tertiary amine catalysts generally are malodorous and offensive and many have high volatility due to their low molecular weight. Release of tertiary amines during foam processing may present significant safety and toxicity problems, and release of residual amines from consumer products is generally undesirable.

Amine catalysts which contain urea functionality have an increase in molecular weight and hydrogen bonding and reduced volatility and odor when compared to related structures which lack this functionality. Furthermore, catalysts which contain urea functionality chemically bond into the urethane during the reaction and are not released from the finished product. Catalyst structures which embody this concept are typically of low to moderate activity and promote both the blowing (water-isocyanate) and the gelling (polyol-isocyanate) reactions to varying extents.

U.S. Pat. No. 4,242,467 discloses the use of morpholino and piperazino substituted ureas as catalysts for producing polyurethane foams.

U.S. Pat. No. 4,644,017 discloses the use of certain diffusion stable amino alkyl ureas having tertiary amino groups in the production of a polyisocyanate addition product which do not discolor or change the constitution of surrounding materials. Specifically taught are Catalyst A and Catalyst D which are reaction products of dimethylaminopropylamine and urea.

U.S. Pat. No. 4,007,140 discloses the use of N,N'-bis(3-dimethylaminopropyl)urea as a low odor catalyst for the manufacture of polyurethanes.

U.S. Pat. No. 4,194,069 discloses the use of N-(3-dimethylaminopropyl)-N'-(3-morpholinopropyl)urea; N,N'-bis(3-dimethylaminopropyl)urea and N, N'-bis(3-morpholinopropyl)urea as catalysts for producing polyurethane foams.

U.S. Pat. No. 4,094,827 discloses the use of certain alkyl substituted ureas including N,N-bis(3-dimethylaminopropyl)urea which provide lower odor and a delay in the foaming reaction that aids in the production of polyurethane foam.

U.S. Pat. No. 4,330,656 discloses the use of N-alkyl ureas as catalysts for the reaction of 1,5-napthylene diisocyanate with polyols or for the chain extension of prepolymers based upon 1,5-napthylene diisocyanate without accelerating atmospheric oxidation.

DE 30 27 796 A discloses the use of higher molecular weight dialkyl aminoalkyl ureas as reduced odor catalysts for the production of polyurethane foam.

EP 499 873 discloses the preparation and use of pyrrolidines as catalysts for the polyisocyanate polyaddition process.

SUMMARY OF THE INVENTION

The present invention provides a reactive catalyst composition for making a water blown flexible polyurethane foam. The catalyst composition comprises a tertiary amino alkyl urea and/or bis(tertiary amino alkyl) urea in combination with either a tertiary amine gelling catalyst or a tertiary amine blowing catalyst. The use of such catalyst composition improves the physical properties of the polyurethane foam.

The reactive catalysts contain ureido functionality which enables the catalyst to react into the polyurethane matrix. These reactive catalysts can be used as gelling catalysts or blowing catalysts with complementary tertiary amine blowing or gelling co-catalysts, respectively, which may or may not contain reactive functional groups to produce polyurethane foam materials. The reactive catalysts produce polyurethane foams which have no amine emissions.

The use of these catalysts in conjunction with complementary gelling or blowing tertiary amine co-catalysts improves physical properties and enhances processibility of the foam. As gelling catalysts, these urea catalysts in conjunction with tertiary amine blowing co-catalysts improve the airflow of the foam. Improved airflow means improved porosity and openness of the foam which is an indication of improved dimensional stability of the foam. As gelling catalysts, these urea catalysts in conjunction with tertiary amine blowing co-catalysts also improve, i.e., reduce, the force-to-crush of the foam. Reduced force-to-crush means the foam is more easily compressed which is an important advantage for minimizing foam shrinkage during processing. As blowing catalysts, these urea catalysts in conjunction with tertiary amine gelling co-catalysts improve the load bearing properties of the foam.

DETAILED DESCRIPTION OF THE INVENTION

The catalyst compositions according to the invention catalyze the reaction between an isocyanate functionality and an active hydrogen-containing compound, i.e. an alcohol, a polyol, an amine or water, especially the urethane (gelling) reaction of polyol hydroxyls with isocyanate to make polyurethanes and the blowing reaction of water with isocyanate to release carbon dioxide for making foamed polyurethanes.

The flexible polyurethane foam products, slab and molded, are prepared using any suitable organic polyisocyanates well known in the art including, for example, hexamethylene diisocyanate, phenylene diisocyanate, toluene diisocyanate ("TDI") and 4,4'-diphenylmethane diisocyanate ("MDI"). Especially suitable are the 2,4- and 2,6-TDI's individually or together as their commercially available mixtures. Other suitable isocyanates are mixtures of diisocyanates known commercially as "crude MDI", marketed as PAPI by Dow Chemical, which contain about 60% of 4,4'-diphenylmethane diisocyanate along with other isomeric and analogous higher polyisocyanates. Also suitable are "prepolymers" of these polyisocyanates comprising a partially prereacted mixture of a polyisocyanate and a polyether or polyester polyol.

Illustrative of suitable polyols as a component of the polyurethane composition are the polyalkylene ether and polyester polyols. The polyalkylene ether polyols include the poly(alkylene oxide) polymers such as poly(ethylene oxide) and poly(propylene oxide) polymers and copolymers with terminal hydroxyl groups derived from polyhydric compounds, including diols and triols; for example, among others, ethylene glycol, propylene glycol, 1,3-butane diol, 1,4-butane diol, 1,6-hexane diol, neopentyl glycol, diethylene glycol, dipropylene glycol, pentaerythritol, glycerol, diglycerol, trimethylol propane and like low molecular weight polyols.

In the practice of this invention, a single high molecular weight polyether polyol may be used. Also, mixtures of high molecular weight polyether polyols such as mixtures of di- and trifunctional materials and/or different molecular weight or different chemical composition materials may be used.

Useful polyester polyols include those produced by reacting a dicarboxylic acid with an excess of a diol, for example, adipic acid with ethylene glycol or butanediol, or reacting a lactone with an excess of a diol such as caprolactone with propylene glycol.

In addition to the polyether and polyester polyols, the masterbatches, or premix compositions, frequently contain a polymer polyol. Polymer polyols are used in polyurethane foam to increase the foam's resistance to deformation, i.e. to increase the load-bearing properties of the foam. Currently, two different types of polymer polyols are used to achieve load-bearing improvement. The first type, described as a graft polyol, consists of a triol in which vinyl monomers are graft copolymerized. Styrene and acrylonitrile are the usual monomers of choice. The second type, a polyurea modified polyol, is a polyol containing a polyurea dispersion formed by the reaction of a diamine and TDI. Since TDI is used in excess, some of the TDI may react with both the polyol and polyurea. This second type of polymer polyol has a variant called PIPA polyol which is formed by the in-situ polymerization of TDI and alkanolamine in the polyol. Depending on the load-bearing requirements, polymer polyols may comprise 20–80% of the polyol portion of the masterbatch.

Other typical agents found in the polyurethane foam formulations include chain extenders such as ethylene glycol and butanediol; crosslinkers such as diethanolamine, diisopropanolamine, triethanolamine and tripropanolamine; blowing agents such as water, CFCs, HCFCs, HFCs, pentane, and the like; and cell stabilizers such as silicones.

A general polyurethane flexible foam formulation having a 1–3 lb/ft$^3$ (16–48 kg/m$^3$) density (e.g., automotive seating) containing a catalyst such as the catalyst composition according to the invention would comprise the following components in parts by weight (pbw):

| Flexible Foam Formulation | pbw |
| --- | --- |
| Polyol | 20–100 |
| Polymer Polyol | 80–0 |
| Silicone Surfactant | 1–2.5 |
| Blowing Agent | 2–4.5 |
| Crosslinker | 0.5–2 |
| Catalyst Composition | 0.5–2 |
| Isocyanate Index | 70–115 |

The catalyst composition comprises a mono(tertiary amino alkyl) urea and/or bis(tertiary amino alkyl) urea in combination with a tertiary amine gelling or blowing catalyst. The mono- and bis-ureas may be represented by the formula

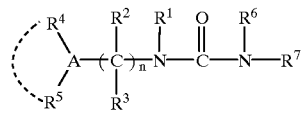

in which

A represents CH or N,

R$^1$ represents hydrogen or the group

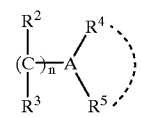

n represents an integer from 1 to 3,

R$^2$ and R$^3$ each represent hydrogen or a C1–C6 alkyl group,

R$^4$ and R$^5$ each represent a C1–C6 alkyl group or together represent a C2–C5 alkylene group which may contain a nitrogen atom (such as NR$^8$ where R$^8$ is hydrogen or a C1–C4 alkyl group) or the group

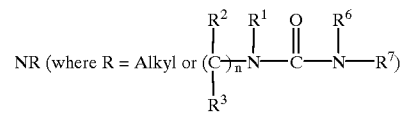

R represents a C1–C4 alkyl group, and

R$^6$ and R$^7$ which may be the same or different each represent hydrogen or the group

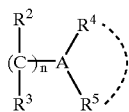

In the above general formula it is preferred that
  $R^1$, $R^2$, $R^3$, $R^6$ and $R^7$ each represent hydrogen,
  $R^4$ and $R^5$ each represent a methyl group when A represents N or together represent $CH_2CH_2N(CH_3)CH_2$ when A represents CH, and
  n represents 1–3, preferably 2 or 3.

Illustrative of suitable mono-ureas and bis-ureas are 2-dimethylaminoethyl urea; N,N'-bis(2-dimethylaminoethyl) urea; N,N-bis(2-dimethylaminoethyl) urea; 3-dimethylaminopropyl urea; N,N'-bis(3-dimethylaminopropyl) urea; N,N-bis(3-dimethylaminopropyl) urea; 1-(N-methyl-3-pyrrolidino)methyl urea; 1,3-bis(N-methyl-3-pyrrolidino)-methyl urea; 3-piperidinopropyl urea; N,N'-bis(3-piperidinopropyl) urea; 2-piperidinoethyl urea; and N,N'-bis(2-piperidinoethyl) urea. U.S. Pat. No. 4,644,017 teaches amino alkyl ureas useful in the practice of the present invention and is hereby incorporated by reference.

The preferred ureas are 3-dimethylaminopropyl urea, N,N'-bis(3-dimethylaminopropyl) urea, 1-(N-methyl-3-pyrrolidino)methyl urea, 1,3-bis(N-methyl-3-pyrrolidino)-methyl urea, a mixture of 3-dimethylaminopropyl urea and N,N'-bis(3-dimethylaminopropyl) urea, and a mixture of 1-(N-methyl-3-pyrrolidino)methyl urea and 1,3-bis(N-methyl-3-pyrrolidino)methyl urea, the mixtures preferably being in a 75:25 to 95:5 molar ratio of mono-urea to bis-urea.

The mono-ureas and bis-ureas are prepared by reacting urea and the corresponding tertiary alkylamine in the appropriate molar ratios under an inert atmosphere at elevated temperatures of from 80° to 150° C., preferably 100° to 130° C., with ammonia being driven off. The mono- and bis-ureas can be isolated individually by chromatographic techniques known in the synthesis art.

The mono-urea and/or bis-urea are used in conjunction with a tertiary amine gelling or a tertiary amine blowing catalyst depending upon the processing advantage desired. The gelling co-catalyst is any tertiary amine catalyst known in the urethane art with an initial selectivity less than about 0.45, and the blowing co-catalyst is any tertiary amine catalyst known in the urethane art with an initial selectivity greater than about 0.8. Catalyst selectivity is defined as the ratio of the rate of blowing (urea formation) to the rate of gelling (urethane formation) [J. Cell. Plastics, Vol. 28, 1992, pp. 360–398.]

Examples of suitable tertiary amine gelling catalysts include but are not restricted to diazabicyclooctane (triethylenediamine), supplied commercially as DABCO 33LV® catalyst by Air Products and Chemicals, Inc., quinuclidine and substituted quinuclidines (U.S. Pat. No. 5,143,944 and U.S. Pat. No. 5,233,039), substituted pyrrolizidines (U.S. Pat. No. 5,512,603), and substituted pyrrolidines (EP 499 873). Examples of suitable tertiary amine blowing catalysts include but are not restricted to bisdimethylaminoethyl ether, commercially supplied as DABCO®) BL-11 catalyst by Air Products and Chemicals, Inc., pentamethyidiethylenetriamine and related compositions (U.S. Pat. No. 5,039,713, U.S. Pat. No. 5,559,161), higher permethylated polyamines (U.S. Pat. No. 4,143,003), branched polyamines (U.S. Pat. No. 3,836,488), 2-[N-(dimethylaminoethoxyethyl)-N-methylamino]ethanol and related structures (U.S. Pat. No. 4,338,408), alkoxylated polyamines (U.S. Pat. No. 5,508,314), imidazole-boron compositions (U.S. Pat. No. 5,539,007), and aminopropyl-bis(aminoethyl)ether compositions (U.S. Pat. No. 5,874,483 and U.S. Pat. No. 5,824,711).

A catalytically effective amount of the catalyst composition comprising the urea and a tertiary amine gelling or blowing catalyst is used in the polyurethane formulation. More specifically, suitable amounts of the catalyst composition may range from about 0.01 to 10 parts by wt per 100 parts polyol (pphp) in the polyurethane formulation, preferably 0.05 to 2 pphp.

The catalyst composition may be used in combination with, or also comprise, other tertiary amine, organotin or carboxylate urethane catalysts well known in the urethane art.

EXAMPLE 1

Blend of 3-Dimethylaminopropyl Urea (I) and N, N'-Bis(3-dimethylaminopropyl) Urea (II)

A 94:6 mole ratio blend of 3-dimethylaminopropyl urea (I) and N,N'-bis(3-dimethylaminopropyl) urea (II) catalyst mixture was prepared using a one liter 3 neck round bottom flask fitted with the following: mechanical stirrer, reflux condenser, nitrogen bubbler, and a temperature controlled heating mantle. The flask was charged with 176.3 g of urea [$CH_4N_2O$] and 300.0 g of N,N-dimethylaminopropylamine [$(CH_3)_2NCH_2CH_2CH_2NH_2$]. The mixture was stirred at a constant rate while being slowly heated to 120° C. The reaction was controlled at 120° C. until all signs of $NH_3$ evolution had ceased (as evidenced by bubbling in the $N_2$ pressure relief device). The pale yellow liquid was cooled to 80° C. and the flask containing the liquid was evacuated via vacuum pump and refilled with $N_2$ three times to remove any volatiles still present. Quantitative $^{13}C$ NMR showed the final product to be 86 mole % 3-dimethylaminopropyl urea (I), 5 mole % N,N'-bis(3-dimethylaminopropyl) urea (II), and 9 mole % unreacted urea. The mono to bis mole ratio is 17.2 to 1, or 94:6 ratio of mono urea to bis urea.

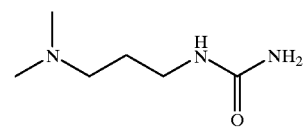

3-Dimethylaminopropyl urea (I)

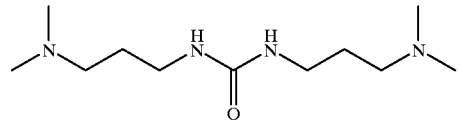

N,N'-Bis(3-dimethylaminopropyl)urea (II)

EXAMPLE 2

Blend of 1-(N-Methyl-3-pyrrolidino)methyl urea (III) and 1,3-Bis(N-methyl-3-pyrrolidino)methyl urea (IV)

A one liter 3 neck round bottom flask was fitted with the following: mechanical stirrer, reflux condenser, nitrogen bubbler, and a temperature controlled heating mantle. The flask was charged with 45.75 g (0.762 mole) of urea ($CH_4N_2O$) and 86.84 g (0.762 mole) of N-methyl-3-aminomethyl pyrrolidine, ($C_6H_{14}N_2$). The mixture was stirred at a constant rate while being slowly heated to 120° C. The reaction was controlled at 120° C. for two hours until all signs of $NH_3$ evolution had ceased (as evidenced by bubbling in the $N_2$ pressure relief device). The pale yellow liquid was cooled to 80° C. and the flask containing the liquid was evacuated via vacuum pump and refilled with $N_2$ three time to remove any volatiles still present. Quantitative $^{13}C$ NMR showed the product to be 81.7 mole % 1-(N-methyl-3-pyrrolidino)methyl urea (III), 7.0 mole % bis(N-methyl-3-pyrrolidino)methyl urea (IV) and 11.3 mole % unreacted urea.

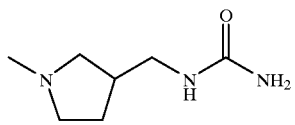

1-(N-Methyl-3-pyrrolidino)methyl urea (III)

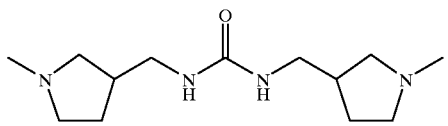

1,3Bis(N-methyl-3-pyrrolidino)methyl urea (IV)

EXAMPLE 3

In this example polyurethane foams were prepared in a conventional manner. The polyurethane formulation in parts by weight was:

| COMPONENT | PARTS |
|---|---|
| E-648 | 60 |
| E-519 | 40 |
| DC-5043 | 1.5 |
| Diethanolamine | 1.49 |
| Water | 3.5 |
| TDI 80 | 105 Index |

E-648 -- a conventional, ethylene oxide tipped polyether polyol from Arco Chemical
E-519 -- a styrene-acrylonitrile copolymer filled polyether polyol from Arco Chemical
DABCO ® DC-5043 -- silicone surfactant marketed by Air Products and Chemicals, Inc.
TDI 80 -- a mixture of 80 wt % 2,4-TDI and 20 wt % 2,6-TDI E-648—a conventional, ethylene oxide tipped polyether polyol from Arco Chemical E-519—a styrene-acrylonitrile copolymer filled polyether polyol from Arco Chemical DABCO® DC-5043—silicone surfactant marketed by Air Products and Chemicals, Inc.

TDI 80—a mixture of 80 wt % 2,4-TDI and 20 wt % 2,6-TDI

Catalyst selectivity is defined as the ratio of the rate of blowing (urea formation) to the rate of gelling (urethane formation) [J. Cell. Plastics, Vol. 28, 1992, pp. 360–398.] A selectivity of "one" means that the amounts of blowing and gelling are equal at that point in the reaction. A selectivity substantially below "one", for example about 0.45, is indicative of a strong gelling catalyst. A selectivity greater than about 0.8 indicates a catalyst with sufficient blowing selectivity to counterbalance a gelling or intermediate selectivity catalyst.

Tables I and II list the physical properties obtained using the catalysts from Examples 1 and 2 in conjunction with industry standard tertiary amine co-catalysts. The foams were made in a heated test block mold at 160° F. (71° C.). In all cases, the foam reactivity was matched by extrusion time which measures reaction progression and provides some indication of extent of cure. The foams tested met standard specifications listed in ASTM D 3453-91 and the physical property tests were performed using ASTM designation D 3574-95. The force-to-crush results were obtained using a mechanical device equipped with a 1000 pound (453.6 kg) capacity pressure transducer mounted between the 50 square inch (322.6 $cm^2$) circular plate and the drive shaft. The Dayton motor specifications, model 4Z528, include 1/6 horsepower (124.3 J/s) with F/L rpm of 1800 and F/L torque of 5.63 in-lb (6.36×$10^4$ Nm). The actual pressure is shown on a digital display. The foam pad is compressed to 50% of its original thickness and the force necessary to achieve the compression is recorded in whole pounds (newtons). A cycle takes 24 seconds to complete and the actual crushing of the foam occurs within 7–8 seconds. This device mimics the ASTM D-3574, Indentation Force Deflection Test, and provides a numerical value for 1 minute post demolded foam initial hardness or softness.

TABLE I

| Catalyst | Use Level (pphp) | Force-to-Crush[a] (lbf; N) |
|---|---|---|
| Example 1 Catalyst / Dabco BL-11 | 0.41/0.10 | 91; 404 |
| Dabco 33LV / Example 1 Catalyst | 0.25/0.31 | 197; 875 |
| Example 2 Catalyst / Dabco BL-11 | 0.24/0.10 | 183; 812 |
| Dabco 33LV / Example 2 Catalyst | 0.25/0.18 | 225; 999 |

[a]Lower force-to-crush values mean the foam is more easily compressed

The first entry in Table I demonstrates that using Example 1 catalyst with Dabco BL-11 blowing catalyst provided lower force-to-crush than the second entry in which Example 1 catalyst was used with Dabco 33LV gelling catalyst. Similarly, entries three and four illustrate that using Example 2 catalyst with Dabco BL-11 blowing catalyst (entry three) also afforded lower force-to-crush values than when Example 2 catalyst was used with Dabco 33LV gelling catalyst (entry four).

TABLE II

| | Dabco 33LV/ Example 1 Catalyst | Dabco 33LV/ Example 2 Catalyst | Example 1 Catalyst Dabco BL-11 | Example 2 Catalyst Dabco BL-11 |
|---|---|---|---|---|
| pphp | 0.25/0.31 | 0.25/0.18 | 0.41/0.10 | 0.24/0.10 |
| Density (lb/$ft^3$; kg/$m^3$) | 2.0; 31.9 | 2.0; 31.9 | 2.0; 32.2 | 2.0; 31.5 |
| Airflow (SCFM; L/min) | 2.86; 81.1 | 3.18; 90.2 | 3.53; 99.8 | 3.30; 93.4 |
| Tensile (psi; kN/$m^2$) | 21.7; 149 | 16.5; 114 | 18.6; 128 | 18.6; 128 |
| Tear (pli; N/cm) | 1.5; 2.6 | 1.5; 2.6 | 1.7; 3.0 | 1.5; 2.6 |

TABLE II-continued

|  | Dabco 33LV/<br>Example 1<br>Catalyst | Dabco 33LV/<br>Example 2<br>Catalyst | Example 1<br>Catalyst<br>Dabco BL-11 | Example 2<br>Catalyst<br>Dabco BL-11 |
| --- | --- | --- | --- | --- |
| Elongation (%) | 88.2 | 99.8 | 107.7 | 103.7 |
| 25% ILD (lbf; N) | 27.0; 119.7 | 27.4; 121.5 | 24.4; 108.2 | 25.5; 112.6 |
| 65% ILD (lbf; N) | 71.9; 319.2 | 70.6; 313.6 | 68.2; 302.9 | 67.1; 297.9 |
| 25% R ILD (lbf; N) | 22.0; 97.9 | 22.5; 99.9 | 19.5; 86.5 | 20.6; 91.3 |
| Ball Rebound (%) | 52 | 52 | 51 | 53 |
| 50% H. A. Comp. Set (%) | 34.7 | 34.4 | 37.3 | 36.6 |
| Japanese Wet Set (%) | 29.4 | 30.9 | 33.0 | 32.7 |

The data in Table II demonstrate that using Example 1 or 2 catalyst with Dabco BL-11 blowing catalyst provided higher airflow and increased elongation than when Example 1 or 2 catalyst is used with Dabco 33LV gelling catalyst. Using Example 1 and 2 catalysts with Dabco 33LV catalyst increased the load bearing properties (ILD) of the foam.

In the prior art cited, the urea-substituted catalysts may be used in conjunction with industry standard co-catalysts such as low levels of weakly active surface cure catalysts or tin gelling catalysts. While such co-catalysts can be used, the prior art does not indicate that certain foam physical properties can be systematically controlled by choice of tertiary amine gelling or blowing co-catalysts in combination with urea-substituted catalysts. Weakly active surface cure tertiary amine catalysts are not tertiary amine gelling or blowing catalysts for purposes of this invention.

The only patents which have an example of a urea-based catalyst used with a tertiary amine co-catalyst are DE 3027796 A1 and U.S. Pat. No. 4,194,069. DE 3027796 A1 discloses the use of higher molecular weight dialkyl aminoalkyl ureas as reduced odor catalysts for the production of polyurethane foam. In this case, a portion (0.3 parts) of the gelling catalyst, diazabicyclooctane, was replaced with the urea catalyst synthesized from hexamethylene diisocyanate and N,N-bis(dimethylaminopropyl) amine (Example A). The results indicated that the foam properties were unchanged, except for lower amine odor (Example 1.2). U.S. Pat. No. 4,194,069 discloses the use of N-(3-dimethylaminopropyl)-N'-(3-morpholinopropyl) urea with the weak tertiary amine blowing catalyst Thancat DD (dimethylaminoethyl dimethylaminopropyl ether). No effect on physical properties of the foam was noted due to the inclusion of the Thancat DD catalyst.

Unexpectedly, Example 3 in the present application demonstrates that foam physical properties can be systematically varied by choosing tertiary amine blowing or gelling co-catalysts. Specifically, physical properties which can be significantly altered are force-to-crush, airflow, elongation and load bearing (ILD).

STATEMENT OF INDUSTRIAL APPLICATION

The invention provides catalyst compositions for making water blown flexible polyurethane foam.

What is claimed is:

1. In a method for preparing a flexible polyurethane foam by reacting an organic polyisocyanate and a polyol in the presence of water as a blowing agent, a cell stabilizer and a catalyst composition, the improvement for reducing the force-to-crush and/or improving airflow of the foam which comprises using a catalyst composition comprising a tertiary amine blowing catalyst which is not a urea compound and a urea catalyst which is at least one compound of the formula

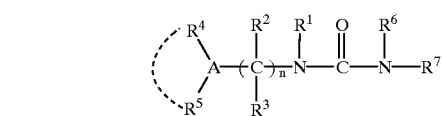

in which

A represents CH or N, $R^1$ represents hydrogen or the group

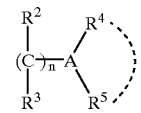

n represents an integer from 1 to 3, $R^2$ and $R^3$ each represent hydrogen or a C1–C6 alkyl group, $R^4$ and $R^5$ each represent a C1–C6 alkyl group or together represent a C2–C5 alkylene group which may contain a heteroatom which is $NR^8$ where $R^8$ is hydrogen or a C1–C4 alkyl group or the group

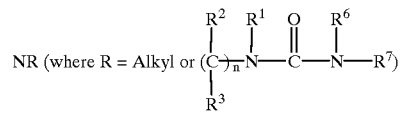

R represents a C1–C4 alkyl group, and $R^6$ and $R^7$ which may be the same or different each represent hydrogen or the group

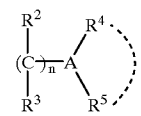

2. The method of claim 1 in which $R^1$, $R^2$, $R^3$, $R^6$ and $R^7$ each represent hydrogen, $R^4$ and $R^5$ each represent a methyl group when A represents N or together represent $CH_2CH_2N(CH_3)CH_2$ when A represents CH, and n represents 1–3.

3. The method of claim 1 in which the urea catalyst is 2-dimethylaminoethyl urea; N, N'-bis(2- dimethylaminoethyl) urea; N,N-bis(2-dimethylaminoethyl) urea; 3-dimethylaminopropyl urea; N,N'-bis(3-dimethylaminopropyl) urea; N, N-bis(3-dimethylaminopropyl) urea; 1-(N-methyl-3-pyrrolidino)methyl urea; 1,3-bis(N-methyl-3-pyrrolidino)methyl urea; 3-piperidinopropyl urea; N,N'-bis(3-piperidinopropyl) urea; 2-piperidinoethyl urea; N,N'-bis(2-piperidinoethyl) urea; or a mixture thereof.

4. The method of claim 1 in which the urea catalyst is 3-dimethylaminopropyl urea, N,N'-bis(3-dimethylaminopropyl) urea, 1-(N-methyl-3-pyrrolidino)methyl urea, 1,3-bis(N-methyl-3-pyrrolidino)methyl urea, a mixture of 3-dimethylaminopropyl urea and N,N'-bis(3-dimethylaminopropyl) urea, or a mixture of 1-(N-methyl-3-pyrrolidino)methyl urea and 1,3-bis(N-methyl-3-pyrrolidino)methyl urea.

5. In a method for making a polyurethane flexible foam having a 1–3 lb/ft³ (16–48 kg/m³) density by reacting the following components in parts by weight (pbw):

| Polyol | 20–100 |
| Polymer Polyol | 80–0 |
| Silicone Surfactant | 1–2.5 |
| Water (Blowing Agent) | 2–4.5 |
| Crosslinker | 0.5–2 |
| Catalyst Composition | 0.5–2 |
| Isocyanate Index | 70–115 | the improvement for reducing the force-to-crush and/or improving airflow of the foam in which the catalyst composition comprises a tertiary amine blowing catalyst which is not a urea compound and a urea catalyst which is at least one compound of the formula

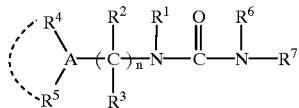

in which

A represents CH or N,

R¹ represents hydrogen or the group

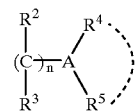

n represents an integer from 1 to 3,

R² and R³ each represent hydrogen or a C1–C6 alkyl group,

R⁴ and R⁵ each represent a C1–C6 alkyl group or together represent a C2–C5 alkylene group which may contain a heteroatom which is NR⁸ where R⁸ is hydrogen or a C1–C4 alkyl group or the group

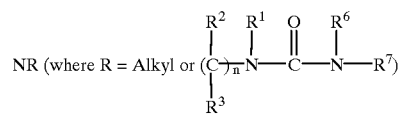

R represents a C1–C4 alkyl group, and

R⁶ and R⁷ which may be the same or different each represent hydrogen or the group

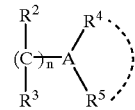

6. The foam composition of claim 5 in which the urea catalyst is 2-dimethylaminoethyl urea; N,N'-bis(2-dimethylaminoethyl) urea; N,N-bis(2-dimethylaminoethyl) urea; 3-dimethylaminopropyl urea; N,N'-bis(3-dimethylaminopropyl) urea; N,N-bis(3-dimethylaminopropyl) urea; 1-(N-methyl-3-pyrrolidino)methyl urea; 1,3-bis(N-methyl-3-pyrrolidino)methyl urea; 3-piperidinopropyl urea; N,N'-bis(3-piperidinopropyl) urea; 2-piperidinoethyl urea; N,N'-bis(2-piperidinoethyl) urea; or a mixture thereof.

* * * * *